United States Patent
Dong et al.

(10) Patent No.: US 11,071,709 B2
(45) Date of Patent: Jul. 27, 2021

(54) ETHANOLIC EXTRACT FROM A PLANT COMPOSITION OF ASTRAGALUS MEMBRANACUS, RADIX SILERIS, RHIZOMA GASTRODIAE, CALENDULA OFFICINALIS, AND ALBIZZIA JULIBRISSIN

(71) Applicant: NUTRI-WOODS BIO-TECH (BEIJING) CO., LTD., Beijing (CN)

(72) Inventors: Yinmao Dong, Beijing (CN); Hankun Ren, Beijing (CN); Hong Meng, Beijing (CN); Yuhong Liu, Beijing (CN); Peina Zha, Beijing (CN)

(73) Assignee: NUTRI-WOODS BIO-TECH (BEIJING) CO., LTD., Beijing (CN)

( * ) Notice: Subject to any disclaimer, the term of this patent is extended or adjusted under 35 U.S.C. 154(b) by 26 days.

(21) Appl. No.: 16/465,947

(22) PCT Filed: Aug. 3, 2017

(86) PCT No.: PCT/CN2017/095772
§ 371 (c)(1),
(2) Date: May 31, 2019

(87) PCT Pub. No.: WO2018/099119
PCT Pub. Date: Jun. 7, 2018

(65) Prior Publication Data
US 2019/0307673 A1      Oct. 10, 2019

(30) Foreign Application Priority Data

Dec. 1, 2016 (CN) .......................... 201611093658.7

(51) Int. Cl.
| | | |
|---|---|---|
| *A61K 36/481* | (2006.01) | |
| *A61K 8/9789* | (2017.01) | |
| *A61K 8/9794* | (2017.01) | |
| *A61K 8/34* | (2006.01) | |
| *A61K 8/36* | (2006.01) | |
| *A61K 8/37* | (2006.01) | |
| *A61K 8/42* | (2006.01) | |
| *A61K 8/49* | (2006.01) | |
| *A61K 8/73* | (2006.01) | |
| *A61K 8/81* | (2006.01) | |
| *A61K 8/891* | (2006.01) | |
| *A61Q 19/00* | (2006.01) | |
| *A61K 8/97* | (2017.01) | |

(52) U.S. Cl.
CPC ............ *A61K 8/9789* (2017.08); *A61K 8/345* (2013.01); *A61K 8/361* (2013.01); *A61K 8/375* (2013.01); *A61K 8/42* (2013.01); *A61K 8/49* (2013.01); *A61K 8/73* (2013.01); *A61K 8/8111* (2013.01); *A61K 8/891* (2013.01); *A61K 8/97* (2013.01); *A61K 8/9794* (2017.08); *A61Q 19/00* (2013.01); *A61Q 19/005* (2013.01); *A61K 2800/5922* (2013.01); *A61K 2800/72* (2013.01); *A61K 2800/805* (2013.01)

(58) Field of Classification Search
None
See application file for complete search history.

(56) References Cited

U.S. PATENT DOCUMENTS

| | | | |
|---|---|---|---|
| 2006/0018867 A1* | 1/2006 | Kawasaki | C08G 77/452 424/70.122 |
| 2009/0104295 A1* | 4/2009 | Kohno | A61K 36/31 424/757 |
| 2016/0106793 A1 | 4/2016 | Peltier et al. | |

FOREIGN PATENT DOCUMENTS

| | | | |
|---|---|---|---|
| CN | 101502540 | * | 8/2009 |
| CN | 105219554 | | 1/2016 |
| CN | 105496917 | | 4/2016 |
| CN | 105770845 | * | 7/2016 |
| CN | 106309200 | | 1/2017 |
| CN | 106420505 | | 2/2017 |

OTHER PUBLICATIONS

Lin, R. et al. Inhibition of Monoamine Oxidase B by Chinese Herbal Medicines. Phytomedicine 10(8)650-656, 2003. (Year: 2003).*
Kim, I. et al. Screening of Estrogenic and Antiestrogenic Activities from Medicinal Plants. Environmental Toxicology and Pharmacology 25(1)75-82, Jan. 2008. (Year: 2008).*
International Search Report dated Oct. 27, 2017 for corresponding PCT Application No. PCT/CN2017/095772.

* cited by examiner

*Primary Examiner* — Ralph J Gitomer
(74) *Attorney, Agent, or Firm* — Duane Morris LLP

(57) ABSTRACT

A traditional Chinese medicine plant composition, comprising in parts by weight: 20-60 parts of *Astragalus membranacus*, 10-30 parts of *Radix sileris*, 10-30 parts of *Rhizoma gastrodiae*, 5-20 parts of *Calendula officinalis*, and 5-15 parts of *Albizzia julibrissin*. The traditional Chinese medicine plant composition has functions of relieving allergies, anti-Allergy itching, eliminating redness and swelling, and allergy recovery, and is safe and does not cause irritation, can be used in skin care products. The traditional Chinese medicine plant composition is prepared by crushing plant raw materials and then extracting same.

3 Claims, 2 Drawing Sheets

ETHANOLIC EXTRACT FROM A PLANT COMPOSITION OF ASTRAGALUS MEMBRANACUS, RADIX SILERIS, RHIZOMA GASTRODIAE, CALENDULA OFFICINALIS, AND ALBIZZIA JULIBRISSIN

CROSS-REFERENCE TO RELATED APPLICATIONS

This application is a U.S. national phase application filed under 35 U.S.C. § 371 of International Application No. PCT/CN2017/095772, which was filed Aug. 3, 2017, and which claims the benefit of the filing date of CN 201611093658.7, which was filed Dec. 1, 2016. The entire content of these applications is hereby incorporated by reference herein.

TECHNICAL FIELD

This application relates to the technical field of daily chemical products, and specifically relates to a traditional Chinese medicine plant composition and a preparation method and use thereof.

BACKGROUND

With acceleration of people's life rhythm, increase of work pressure and changes in diet structure, allergic people are growing rapidly. According to incomplete statistics, allergic patients account for two-fifths of the world's population. On a global scale, there are more and more people who personally feel allergic skin. Skin allergies have become a social problem affecting human health, and thus a hot issue studied by scholars.

At present, the development of natural anti-allergic additives mostly achieves anti-allergic effects by a single anti-inflammatory pathway, which can comprehensively improve skin sensitivity to some extent, however, it cannot satisfy such skin care appeal of consumers that the sensitive state of the skin is expected to be systematically improved from the perspective of "Skin well-being".

Research and development of special plant functional raw materials by combining traditional Chinese medicine theory with modern science and technology, which are guided by the systematic view, based on dermatology, and combined with the attributes of cosmetics, possesses unique advantages. Traditional Chinese medicine believes that skin sensitivity is because of attack of "Wind, Dampness, Heat, Toxin" on the skin. Accordingly, in combination with the expositions of the ancients such as "Wind should be treated by regulating Blood disorder, and Wind disappears after activating Blood", drawing the inspiration from the traditional formulations including "Yupingfeng powder formulation" etc., thinking about the new thought of plant functional raw materials for anti-allergic cosmetics with the principle of defending barrier and enhancing superficial resistance, expelling pathogenic Wind and dissipating pathogens, has realistic significance and broad market prospects.

There are also some anti-Allergy products on the market. CN105287280A discloses a plant soothing agent and a preparation method thereof, wherein the product is prepared by mixing licorice, *Artemisia apiacea, Radix gentianae, Radix sophorae flavescentis* and *Fructus cnidii* in proportion, and by extraction, filtration and concentration, wherein, an expanded bed and a fixed bed are used in succession in the extraction, while the filtration comprises coarse filtration by a microporous membrane and ultrafiltration by an ultrafiltration membrane, and finally the nanofiltration is used for the concentration. This invention is expensive in equipment, complicated in operation, and cannot readily be implemented.

CN105769654A discloses a soothing skin care composition and application thereof in cosmetics, wherein the product is prepared by mixing *Opuntia dillenii, Herba portulacae, Barbados aloe, Hydrocotyle asiatica* and *Tremella fuciformis* in proportion, and by steps such as heat reflux extraction, filtration and reconstitution. Wherein, the raw materials need to be pretreated, and the tremella fuciformis extract is treated separately from other extracts, which increases the preparation difficulty and complicates the process.

CN104784466A discloses an external traditional Chinese medicine composition having allergy-relieving and anti-irritation functions and a preparation method thereof, wherein the product is prepared by mixing *Bignonia grandiflora*, muskmelon root, *Adenophora stricta, Opuntia dillenii, Radix sophorae* flavescentis, *Ophiopogon japonicas*, Sweet tea (*Rubus suavissimis*) leaf in proportion, and by steps such as extraction, filteration and redissolvation. However, this invention adopts a large variety of raw materials, and has a complex composition and high cost.

Most of the above inventions only achieve the functions of relieving allergies and relieving itching, and the types of raw materials are numerous and complex, however, the single function cannot meet the demands of people, moreover, the preparation process is complicated and the equipment is expensive, and all of these inventions are not verified by safety tests and thus have certain risk.

SUMMARY

In order to solve the above technical problems, the present invention provides a traditional chinese medicine plant composition and a preparation method and use thereof. The present invention has functions of relieving allergies, soothing itching, eliminating redness and swelling, and allergy recovery by employing the dsynergistic effects of the five components including stragalus membranacus, *Radix sileris, Rhizoma gastrodiae, Calendula officinalis* and *Albizzia julibrissin*, and the traditional Chinese medicine plant composition in the present application is safe and does not cause irritation, can be used in skin care products.

To achieve this purpose, the present invention adopts the following technical solutions:

In a first aspect, the present invention provides a traditional Chinese medicine plant composition, comprising in parts by weight: 20-60 parts of *Astragalus membranacus*, 10-30 parts of *Radix sileris*, 10-30 parts of *Rhizoma gastrodiae*, 5-20 parts of *Calendula officinalis*, and 5-15 parts of *Albizzia julibrissin*.

The present invention has functions of relieving allergies, soothing itching, eliminating redness and swelling, and allergy recovery by employing the mutual promotion and dsynergistic effects of the five components including stragalus membranacus, *Radix sileris, Rhizoma gastrodiae, Calendula officinalis* and *Albizzia julibrissin*.

According to the present invention, the stragalus membranacus, *Radix sileris, Rhizoma gastrodiae, Calendula officinalis* and *Albizzia julibrissin* are all widely planted and those well-known in the art, different sources of varieties of stragalus membranacus, *Radix sileris, Rhizoma gastrodiae, Calendula officinalis* and *Albizzia julibrissin* will not cause differences in efficacy of traditional Chinese medicine plant composition, and do not affect the traditional Chinese medicine plant composition of the present invention.

According to the present invention, the weight parts of the *Scutellaria scutellariae* in the traditional Chinese medicine plant composition are 20-60 parts and may be, for example, 20 parts, 21 parts, 22 parts, 23 parts, 24 parts, 25 parts, 26 parts, 27 parts, 28 parts, 29 parts, 30 parts, 31 parts, 32 parts, 33 parts, 34 parts, 35 parts, 36 parts, 37 parts, 38 parts, 39 parts, 40 parts, 41 parts, 42 parts, 43 parts, 44 parts, 45 parts, 46 parts, 47 parts, 48 parts, 49 parts, 50 parts, 51 parts, 52 parts, 53 parts, 54 parts, 55 parts, 56 parts, 57 parts, 58 parts, 59 parts or 60 parts, preferably 30-50 parts, further preferably 35-45 parts, and specific point values between the above values, and the specific point values included in said ranges are not exhaustively illustrated by the present invention for the sake of brevity and for the sake of clarity and simplicity.

According to the present invention, the weight parts of the *Radix sileris* in the traditional Chinese medicine plant composition are 10-30 parts and may be, for example, 10 parts, 11 parts, 13 parts, 14 parts, 15 parts, 16 parts, 17 parts, 18 parts, 19 parts, 20 parts, 21 parts, 22 parts, 23 parts, 24 parts, 25 parts, 26 parts, 27 parts, 28 parts, 29 parts or 30 parts, preferably 15-25 parts, further preferably 18-25 parts, and specific point values between the above values, and the specific point values included in said ranges are not exhaustively illustrated by the present invention for the sake of brevity and for the sake of clarity and simplicity.

According to the present invention, the weight parts of the *Rhizoma gastrodiae* in the traditional Chinese medicine plant composition are 10-30 parts and may be, for example, 10 parts, 11 parts, 13 parts, 14 parts, 15 parts, 16 parts, 17 parts, 18 parts, 19 parts, 20 parts, 21 parts, 22 parts, 23 parts, 24 parts, 25 parts, 26 parts, 27 parts, 28 parts, 29 parts or 30 parts, preferably 15-25 parts, further preferably 18-25 parts, and specific point values between the above values, and the specific point values included in said ranges are not exhaustively illustrated by the present invention for the sake of brevity and for the sake of clarity and simplicity.

According to the present invention, the weight parts of the *Calendula officinalis* in the traditional Chinese medicine plant composition are 5-20 parts and may be, for example, 5 parts, 6 parts, 8 parts, 9 parts, 10 parts, 11 parts, 12 parts, 13 parts, 14 parts, 15 parts, 16 parts, 17 parts, 18 parts, 19 parts or 20 parts, preferably 8-15 parts, further preferably 12-15 parts, and specific point values between the above values, and the specific point values included in said ranges are not exhaustively illustrated by the present invention for the sake of brevity and for the sake of clarity and simplicity.

According to the present invention, the weight parts of the *Albizzia julibrissin* in the traditional Chinese medicine plant composition are 5-15 parts and may be, for example, 5 parts, 6 parts, 8 parts, 9 parts, 10 parts, 11 parts, 12 parts, 13 parts, 14 parts or 15 parts, preferably 5-10 parts, further preferably 6-10 parts, and specific point values between the above values, and the specific point values included in said ranges are not exhaustively illustrated by the present invention for the sake of brevity and for the sake of clarity and simplicity.

In a second aspect, the present invention provides a preparation method of the traditional Chinese medicine plant composition according to the first aspect, which preparation method comprises the following steps:

(1) crushing plant raw materials and then evenly blending according to formula amounts.

(2) extracting the blended raw materials obtained in the step (1) by reflux with 95% ethanol, cooling to below 30° C., and conducting vacuum suction filtration;

(3) evaporating filtered section obtained in the step (2), adding 1,3-butanediol, cooling to below 30° C., and conducting vacuum suction filtration; and (4) sterilizing the filtered section obtained in the step (3), cooling to below 30° C. to prepare the traditional Chinese medicine plant composition.

The crushing in the step (1) is aimed at a mesh count of 6-200 mesh, may for example, 6 mesh, 7 mesh, 8 mesh, 9 mesh, 10 mesh, 12 mesh, 15 mesh, 16 mesh, 18 mesh, 20 mesh, 22 mesh, 25 mesh, 26 mesh, 28 mesh, 30 mesh, 35 mesh, 40 mesh, 45 mesh, 50 mesh, 60 mesh, 70 mesh, 80 mesh, 90 mesh, 100 mesh, 110 mesh, 120 mesh, 130 mesh, 140 mesh, 150 mesh, 160 mesh, 170 mesh, 180 mesh, 190 mesh or 200 mesh, preferably 10-100 mesh, and specific point values between the above values, and the specific point values included in said ranges are not exhaustively illustrated by the present invention for the sake of brevity and for the sake of clarity and simplicity.

The mass to volume ratio of the raw materials to the ethanol in the step (2) is 1:(8-30), and may be, for example, 1:8, 1:9, 1:10, 1:11, 1:12, 1:13, 1:14, 1:15, 1:16, 1:17, 1:18, 1:19 1, 20, 1:21, 1:22, 1:23, 1:24, 1:25, 1:26, 1:27, 1:28, 1:29 or 1:30, preferably 1:(10-15); and specific point values between the above values, and the specific point values included in said ranges are not exhaustively illustrated by the present invention for the sake of brevity and for the sake of clarity and simplicity.

Preferably, the temperature for the extraction by reflux in the step (2) is 80-85° C., and may be, for example, 80° C., 81° C., 82° C., 83° C., 84° C., 85° C., and specific point values between the above values, and the specific point values included in said ranges are not exhaustively illustrated by the present invention for the sake of brevity and for the sake of clarity and simplicity.

Preferably, the time for the extraction by reflux in the step (2) is 90-120 min, and may be, for example, 90 min, 91 min, 92 min, 93 min, 94 min, 95 min, 96 min, 98 min, 100 min, 102 min, 103 min, 105 min, 106 min, 108 min, 110 min, 112 min, 113 min, 114 min, 115 min, 116 min, 118 min, 120 min, preferably 95-115 min, and specific point values between the above values, and the specific point values included in said ranges are not exhaustively illustrated by the present invention for the sake of brevity and for the sake of clarity and simplicity.

Preferably, the evaporation in the step (3) is carried out by means of rotary evaporation.

Preferably, the temperature for the rotary evaporation is 40-80° C., preferably 50-60° C., and may be, for example, 40° C., 41° C., 42° C., 43° C., 45° C., 46° C., 48° C., 50° C., 51° C., 52° C., 53° C., 55° C., 56° C., 58° C., 60° C., 61° C., 63° C., 65° C., 68° C., 70° C., 71° C., 73° C., 75° C., 78° C., 80° C., and specific point values between the above values, and the specific point values included in said ranges are not exhaustively illustrated by the present invention for the sake of brevity and for the sake of clarity and simplicity.

Preferably, the mass ratio of the filtered section to the 1,3-butanediol is 1:(0.5-3), and may be, for example, 1:0.5, 1:0.6, 1:0.7, 1:0.8, 1:1, 1:1.2, 1:1.3, 1:1.5, 1:1.6, 1:1.8, 1:2, 1:2.1, 1:2.3, 1:2.5, 1:2.6, 1:2.8, 1:3, preferably 1:(1-2), further preferably 1:1, and specific point values between the above values, and the specific point values included in said ranges are not exhaustively illustrated by the present invention for the sake of brevity and for the sake of clarity and simplicity.

Preferably, the temperature for the sterilization in the step (4) is 80-100° C., and may be, for example, 80° C., 81° C., 82° C., 83° C., 84° C., 85° C., 86° C., 88° C., 90° C., 91°

C., 93° C., 95° C., 96° C., 98° C. or 100° C., preferably 85-90° C., and specific point values between the above values, and the specific point values included in said ranges are not exhaustively illustrated by the present invention for the sake of brevity and for the sake of clarity and simplicity.

Preferably, the time for the sterilization in the step (4) is 20-60 min, and may be, for example, 20 min, 21 min, 23 min, 25 min, 26 min, 28 min, 30 min, 31 min, 33 min, 35 min, 36 min, 38 min, 40 min, 41 min, 42 min, 43 min, 45 min, 48 min, 50 min, 51 min, 53 min, 55 min, 58 min or 60 min, preferably 30-50 min, and specific point values between the above values, and the specific point values included in said ranges are not exhaustively illustrated by the present invention for the sake of brevity and for the sake of clarity and simplicity.

In a third aspect, the present invention provides a skin care product, comprising the traditional Chinese medicine plant composition according to the first aspect or the traditional Chinese medicine plant composition prepared by the preparation method according to the second aspect.

Preferably, the plant composition accounts for 0.5-10% by mass of the skin care product, and may, for example, 0.5%, 0.6%, 0.7%, 0.8%, 1%, 3%, 4%, 5%, 6%, 7%, 8%, 9% or 10%, preferably 1-5% by mass, and specific point values between the above values, and the specific point values included in said ranges are not exhaustively illustrated by the present invention for the sake of brevity and for the sake of clarity and simplicity.

According to the present invention, the skin care product further comprises an adjuvant.

Preferably, the adjuvant is an adjuvant phase A, an adjuvant phase B, and an adjuvant phase C.

Preferably, the adjuvant phase A is xanthan gum and/or glyceryl.

Preferably, the adjuvant phase B is a mixture of glyceryl stearate/PEG-100 stearate, cetearyl alcohol, pentaerythritol distearate, hydrogenated polyisobutylene, caprylic/capric triglyceride, poly dimethyl silicon and isostearyl isostearate.

Preferably, the adjuvant phase C is a mixture of methyl isothiazolinone/iodopropynyl butylcarbamate and phenoxyethanol/ethylhexylglycerin.

According to the present invention, the adjuvant phase A comprises in percentages by mass: 0.02-0.08% of xanthan gum and 1.5-3% of glyceryl.

The xanthan gum may be, for example, 0.02%, 0.03%, 0.04%, 0.05%, 0.06%, 0.07% or 0.08%, and specific point values between the above values, and the specific point values included in said ranges are not exhaustively illustrated by the present invention for the sake of brevity and for the sake of clarity and simplicity.

The glyceryl may be, for example, 1.5%, 1.6%, 1.7%, 1.8%, 2%, 2.1%, 2.3%, 2.5%, 2.6%, 2.8% or 3%, and specific point values between the above values, and the specific point values included in said ranges are not exhaustively illustrated by the present invention for the sake of brevity and for the sake of clarity and simplicity.

Preferably, the adjuvant phase B comprises in percentages by mass:

| | |
|---|---|
| glyceryl stearate/PEG-100 stearate | 2-3% |
| cetearyl alcohol | 0.5-1.5% |
| pentaerythritol distearate | 1-2% |
| hydrogenated polyisobutylene | 2-4% |
| caprylic/capric triglyceride | 2-4% |
| poly dimethyl silicon | 1-3% |
| isostearyl isostearate | 2-4%; |

The glyceryl stearate/PEG-100 stearate may be, for example, 2%, 2.1%, 2.2%, 2.3%, 2.4%, 2.5%, 2.6%, 2.7%, 2.8%, 2.9%, 3%, and specific point values between the above values, and the specific point values included in said ranges are not exhaustively illustrated by the present invention for the sake of brevity and for the sake of clarity and simplicity.

The cetearyl alcohol may be, for example, 0.5%, 0.6%, 0.7%, 0.8%, 0.9%, 1%, 1.1%, 1.2%, 1.3%, 1.4%, 1.5%, and specific point values between the above values, and the specific point values included in said ranges are not exhaustively illustrated by the present invention for the sake of brevity and for the sake of clarity and simplicity.

The pentaerythritol distearate may be, for example, 1%, 1.1%, 1.2%, 1.3%, 1.4%, 1.5%, 1.6%, 1.7%, 1.8%, 1.9%, 2%, and specific point values between the above values, and the specific point values included in said ranges are not exhaustively illustrated by the present invention for the sake of brevity and for the sake of clarity and simplicity.

The hydrogenated polyisobutylene may be, for example, 2%, 2.1%, 2.2%, 2.3%, 2.4%, 2.5%, 2.6%, 2.7%, 2.8%, 2.9%, 3%, 3.1%, 3.2%, 3.3%, 3.5%, 3.6%, 3.8%, 4%, and specific point values between the above values, and the specific point values included in said ranges are not exhaustively illustrated by the present invention for the sake of brevity and for the sake of clarity and simplicity.

The caprylic/capric triglyceride may be, for example, 2%, 2.1%, 2.2%, 2.3%, 2.4%, 2.5%, 2.6%, 2.7%, 2.8%, 2.9%, 3%, 3.1%, 3.2%, 3.3%, 3.5%, 3.6%, 3.8%, 4%, and specific point values between the above values, and the specific point values included in said ranges are not exhaustively illustrated by the present invention for the sake of brevity and for the sake of clarity and simplicity.

The poly dimethyl silicon may be, for example, 1%, 1.1%, 1.2%, 1.3%, 1.4%, 1.5%, 1.6%, 1.7%, 1.8%, 1.9%, 2%, 2.1%, 2.2%, 2.3%, 2.5%, 2.6%, 2.8%, 3%, and specific point values between the above values, and the specific point values included in said ranges are not exhaustively illustrated by the present invention for the sake of brevity and for the sake of clarity and simplicity.

The isostearyl isostearate may be, for example, 2%, 2.1%, 2.2%, 2.3%, 2.4%, 2.5%, 2.6%, 2.7%, 2.8%, 2.9%, 3%, 3.1%, 3.2%, 3.3%, 3.5%, 3.6%, 3.8%, 4%, and specific point values between the above values, and the specific point values included in said ranges are not exhaustively illustrated by the present invention for the sake of brevity and for the sake of clarity and simplicity.

Preferably, the adjuvant phase C comprises in percentages by mass:

| | |
|---|---|
| methyl isothiazolinone/iodopropynyl butylcarbamate | 0.02-0.08% |
| phenoxyethanol/ethylhexylglycerin | 0.2-0.8%. |

The methyl isothiazolinone/iodopropynyl butylcarbamate may be, for example, 0.02%, 0.03%, 0.04%, 0.05%, 0.06%, 0.07%, 0.08%, and specific point values between the above values, and the specific point values included in said ranges are not exhaustively illustrated by the present invention for the sake of brevity and for the sake of clarity and simplicity.

The phenoxyethanol/ethylhexylglycerin may be, for example, 0.2%, 0.3%, 0.4%, 0.5%, 0.6%, 0.7%, 0.8%, and specific point values between the above values, and the specific point values included in said ranges are not exhaustively illustrated by the present invention for the sake of brevity and for the sake of clarity and simplicity.

As a preferred technical solution, the skin care product comprises in percentages by mass:

| the adjuvant phase A: | |
| --- | --- |
| xanthan gum | 0.02-0.08% |
| glyceryl | 1.5-3% |
| the adjuvant phase B: | |
| glyceryl stearate/PEG-100 stearate | 2-3% |
| cetearyl alcohol | 0.5-1.5% |
| pentaerythritol distearate | 1-2% |
| hydrogenated polyisobutylene | 2-4% |
| caprylic/capric triglyceride | 2-4% |
| poly dimethyl silicon | 1-3% |
| isostearyl isostearate | 2-4% |
| the adjuvant phase C: | |
| methyl isothiazolinone/iodopropynyl butylcarbamate | 0.02-0.08% |
| phenoxyethanol/ethylhexylglycerin | 0.2-0.8%; |
| the traditional Chinese medicine plant composition according to the first aspect with the balance being water. | 0.5-10%; |

In a fourth aspect, the present invention provides a preparation method of the skin care product according to the third aspect, comprising the following steps:

(1) adding the xanthan gum in the adjuvant phase A to the glyceryl and evenly blending, and heating to 80-85° C.;

(2) mixing the raw materials of the adjuvant phase B, and heating to 80-85° C.;

(3) adding all the adjuvant phase B of the step (2) to adjuvant phase A of the step (1), homogenizing at 2000-3000 r/min for 5-10 min, heating to 80° C. and stirring for 20-40 min, then starting cooling at a cooling rate of 1-2° C./min by stirring at a stirring rate of 30-50 r/min; and (4) when the temperature is lowered to 45-50° C., adding the adjuvant phase C and the traditional Chinese medicine plant composition according to claim 1 or 2, stirring evenly, and continuing to cool to below 38° C. to obtain the skin care product.

As compared to the existing technologies, the present invention has at least the following beneficial effects:

(1) The traditional Chinese medicine plant composition in the present invention has functions of relieving allergies, soothing itching, eliminating redness and swelling, and allergy recovery by employing the mutual promotion and dsynergistic effects of the five components including stragalus membranacus, *Radix sileris, Rhizoma gastrodiae, Calendula officinalis* and *Albizzia julibrissin*, and is safe and does not cause irritation;

(2) The traditional Chinese medicine plant composition of the present invention can be used as a raw material for skin care products, which is safe and reliable, and does not cause irritation to the skin and eyes, and possesses multiple anti-Allergy and improving effects of relieving itching, eliminating redness, eliminating swelling, anti-Allergy improvements antipruritic, blushing, swelling, reducing tingling and tension while skin care;

(3) The preparation method of the traditional Chinese medicine plant composition of the present invention is simple, low in cost, and conducive to industrialized production, which lays a foundation for marketization.

DETAILED DESCRIPTION

Figure 1:
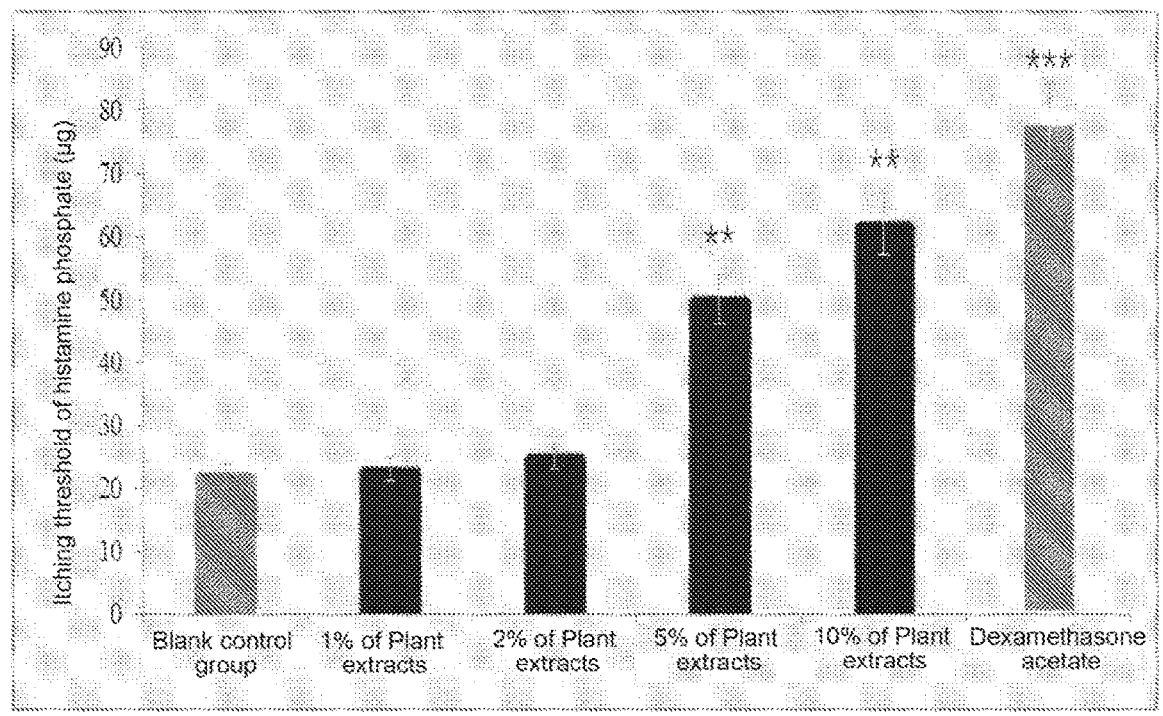
FIG. 1 shows the effect of the traditional Chinese medicine plant composition on the itching threshold of guinea pigs tolerant to histamine phosphate, wherein ** indicates the analysis by SPSS Dunnett-t test is employed.

In order to facilitate the understanding of the present invention, some examples are set forth herein below. Those skilled in the art shall understand that the embodiments are set forth to assist in understanding the present invention and should not be regarded as specific limitations to the present invention.

Example 1

A preparation method of the traditional Chinese medicine plant composition, comprising the following steps:

(1) 40 parts of *Astragalus membranaceus*, 20 parts of *Radix sileris*, 20 parts of *Rhizoma gastrodiae*, 12 parts of *Calendula officinalis*, and 8 parts of *Albizzia julibrissin* as plant raw materials were crushed to 50 mesh and blended evenly;

(2) the blended raw materials according to step (1) were reflux-extracted at a mass-to-volume ratio of 1:13 to 95% ethanol for heat reflux extraction at 80° C. for 120 min, cooled to below 30° C., and subjected to vacuum suction filtration;

(3) the filtered section obtained in the step (2) was injected to a rotary evaporator flask, and all the ethanol was rotary evaporated at 55° C., 1,3-butanediol was added in a mass ratio of 1:1 to the mixture, cooled to below 30° C., and subjected to vacuum suction filtration;

(4) the filtered section obtained in the step (3) was heat sterilized with a water-bath pot at 87° C. for 30 min, cooled to below 30° C. to prepare the traditional Chinese medicine plant composition.

Example 2

A preparation method of the traditional Chinese medicine plant composition, comprising the following steps:

(1) 35 parts of *Astragalus membranaceus*, 18 parts of *Radix sileris*, 18 parts of *Rhizoma gastrodiae*, 12 parts of *Calendula officinalis*, and 6 parts of *Albizzia julibrissin* as plant raw materials were crushed to 80 mesh and blended evenly;

(2) the blended raw materials according to step (1) were reflux-extracted at a mass-to-volume ratio of 1:10 to 95% ethanol for heat reflux extraction at 82° C. for 100 min, cooled to below 30° C., and vacuum subjected to suction filtration; (3) the filtered section obtained in the step (2) was injected to a rotary evaporator flask, and all the ethanol was rotary evaporated at 50° C., 1,3-butanediol was added in a mass ratio of 1:2 to the mixture, cooled to below 30° C., and subjected to vacuum suction filtration;

(4) the filtered section obtained in the step (3) was heat sterilized with a water-bath pot at 85° C. for 50 min, cooled to below 30° C. to prepare the traditional Chinese medicine plant composition.

Example 3

A preparation method of the traditional Chinese medicine plant composition, comprising the following steps:

(1) 45 parts of *Astragalus membranaceus*, 25 parts of *Radix sileris*, 25 parts of *Rhizoma gastrodiae*, 15 parts of *Calendula officinalis*, and 10 parts of *Albizzia julibrissin* as plant raw materials were crushed to 10 mesh and blended evenly;

(2) the blended raw materials according to step (1) were reflux-extracted at a mass-to-volume ratio of 1:20 to 95% ethanol for heat reflux extraction at 85° C. for 120 min, cooled to below 30° C., and subjected to vacuum suction filtration;

(3) the filtered section obtained in the step (2) was injected to a rotary evaporator flask, and all the ethanol was rotary evaporated at 80° C., 1,3-butanediol was added in a mass ratio of 1:3 to the mixture, cooled to below 30° C., and subjected to vacuum suction filtration;

(4) the filtered section obtained in the step (3) was heat sterilized with a water-bath pot at 100° C. for 20 min, cooled to below 30° C. to prepare the traditional Chinese medicine plant composition.

Example 4

A preparation method of the traditional Chinese medicine plant composition, comprising the following steps:

(1) 30 parts of *Astragalus membranaceus*, 15 parts of *Radix sileris*, 15 parts of *Rhizoma gastrodiae*, 10 parts of *Calendula officinalis*, and 5 parts of *Albizzia julibrissin* as plant raw materials were crushed to 100 mesh and blended evenly;

(2) the blended raw materials according to step (1) were reflux-extracted at a mass-to-volume ratio of 1:10 to 95% ethanol for heat reflux extraction at 82° C. for 100 min, cooled to below 30° C., and subjected to vacuum suction filtration;

(3) the filtered section obtained in the step (2) was injected to a rotary evaporator flask, and all the ethanol was rotary evaporated at 50° C., 1,3-butanediol was added in a mass ratio of 1:1 to the mixture, cooled to below 30° C., and subjected to vacuum suction filtration;

(4) the filtered section obtained in the step (3) was heat sterilized with a water-bath pot at 85° C. for 40 min, cooled to below 30° C. to prepare the traditional Chinese medicine plant composition.

Example 5

A preparation method of the traditional Chinese medicine plant composition, comprising the following steps:

(1) 20 parts of *Astragalus membranaceus*, 10 parts of *Radix sileris*, 10 parts of *Rhizoma gastrodiae*, 5 parts of *Calendula officinalis*, and 5 parts of *Albizzia julibrissin* as plant raw materials were crushed to 6 mesh and blended evenly;

(2) the blended raw materials according to step (1) were reflux-extracted at a mass-to-volume ratio of 1:8 to 95% ethanol for heat reflux extraction at 85° C. for 120 min, cooled to below 30° C., and subjected to vacuum suction filtration;

(3) the filtered section obtained in the step (2) was injected to a rotary evaporator flask, and all the ethanol was rotary evaporated at 40° C., 1,3-butanediol was added in a mass ratio of 1:0.5 to the mixture, cooled to below 30° C., and subjected to vacuum suction filtration;

(4) the filtered section obtained in the step (3) was heat sterilized with a water-bath pot at 100° C. for 20 min, cooled to below 30° C. to prepare the traditional Chinese medicine plant composition.

Example 6

A preparation method of the traditional Chinese medicine plant composition, comprising the following steps:

(1) 60 parts of *Astragalus membranaceus*, 30 parts of *Radix sileris*, 30 parts of *Rhizoma gastrodiae*, 20 parts of *Calendula officinalis*, and 15 parts of *Albizzia julibrissin* as plant raw materials were crushed to 200 mesh and blended evenly;

(2) the blended raw materials according to step (1) were reflux-extracted at a mass-to-volume ratio of 1:30 to 95% ethanol for heat reflux extraction at 80° C. for 90 min, cooled to below 30° C., and subjected to vacuum suction filtration;

(3) the filtered section obtained in the step (2) was injected to a rotary evaporator flask, and all the ethanol was rotary evaporated at 80° C., 1,3-butanediol was added in a mass ratio of 1:3 to the mixture, cooled to below 30° C., and subjected to vacuum suction filtration;

(4) the filtered section obtained in the step (3) was heat sterilized with a water-bath pot at 80° C. for 60 min, cooled to below 30° C. to prepare the traditional Chinese medicine plant composition.

Comparison Example 1

The same as Example 1 except for no *Astragalus membranaceus*, 30 parts of *Radix sileris*, 30 parts of *Rhizoma gastrodiae*, 20 parts of *Calendula officinalis*, and 20 parts of *Albizzia julibrissin*.

Comparison Example 2

The same as Example 1 except for no *Radix sileris*, 50 parts of *Astragalus membranaceus*, 30 parts of *Rhizoma gastrodiae*.

Comparison Example 3

The same as Example 1 except for no *Rhizoma gastrodiae*, 50 parts of *Astragalus membranaceus*, 30 parts of *Radix sileris*.

Comparison Example 4

The same as Example 1 except for no *Calendula officinalis*, 52 parts of *Astragalus membranaceus*.

Comparison Example 5

The same as Example 1 except for no *Albizzia julibrissin*, 48 parts of *Astragalus membranaceus*.

Comparison Example 6

The same as Example 1 except for 15 parts of *Astragalus membranaceus*, 5 parts of *Radix sileris*, 5 parts of *Rhizoma gastrodiae*, 3 parts of *Calendula officinalis*, and 3 parts of *Albizzia julibrissin*.

Comparison Example 7

The same as Example 1 except for 65 parts of *Astragalus membranaceus*, 35 parts of *Radix sileris*, 35 parts of *Rhizoma gastrodiae*, 25 parts of *Calendula officinalis*, and 20 parts of *Albizzia julibrissin*.

The relevant tests were carried out on Examples 1-6, Comparative Examples 1-7 and commercially available products, and the tests are as follows:

(1) Anti-Allergy Itching-Inhibiting Itching Caused by Histamine

Histamine, which acts as a chemical delivery substance in mast cells, plays an important role in the development of anaphylactic diseases or inflammation in the body. Itching is a symptom of cutaneous anaphylaxis and is also associated with the release of histamine by local mast cells, accordingly, the model, where endogenous histamine released by inducing with exogenous histamine causes skin itching, can be used to test the abilities of the compositions to render animals resistant to histamine, and to further evaluate the antipruritic and anti-allergic effects of the traditional Chinese medicine plant compositions.

Histamine phosphate that has a higher itching threshold indicates that it has a better anti-allergic effect.

One day before the test, the samples were applied to the right hind paw dorsum of each group of guinea pigs once. On the day of the test, a shaved portion of the right hind paw of the animal was abraded with a coarse sandpaper by about 1 cm$^2$, and the samples were applied thereto once, while the blank control group was given an equal amount of distilled water. After 10 min, the corresponding concentration of histamine phosphate was added dropwise at the abrasion, and then the concentration was incremented sequentially increased every 3 min until the guinea pig turned back to lick its right hind paw, and the total amount of histamine phosphate dropped when finally the guinea pig turned back to lick its right hind paw was considered as the itching threshold.

The results are shown in FIG. 1 and Table 1. In FIG. 1, Example 1 was used as the test product group, and the test product group was applied with different concentrations of 1%, 2%, 5% and 10%, and the test comprises blank control group and positive control group (dexamethasone acetate), after applying the test product to the itching site, the traditional Chinese medicine plant composition with a concentration of 5% and 10% can significantly increase the itching threshold of histamine phosphate in guinea pigs, which has a significant difference when compared with the blank in the control group (P<0.01), moreover, the itching threshold is proportional to the addition amount of the traditional Chinese medicine plant composition.

In Examples 1-6 and Comparative Examples 1-7 in Table 1, the traditional Chinese medicine plant composition was applied to the itching site at a concentration of 5%, and the results are shown in Table 1:

TABLE 1

| | Itching threshold of histamine phosphate (µg) |
|---|---|
| Example 1 | 57 |
| Example 2 | 55 |
| Example 3 | 53 |
| Example 4 | 50 |
| Example 5 | 48 |
| Example 6 | 47 |
| Comparison Example 1 | 26 |
| Comparison Example 2 | 30 |
| Comparison Example 3 | 31 |
| Comparison Example 4 | 32 |
| Comparison Example 5 | 33 |
| Comparison Example 6 | 35 |
| Comparison Example 7 | 37 |

As can be seen from Table 1, compared with Comparison Examples 1-7, the itching threshold of histamine phosphate was greatly improved Examples 1-6 by adjusting the ratio of the five components of *Astragalus membranacus*, *Radix sileris*, *Rhizoma gastrodiae*, *Calendula officinalis* and *Albizzia julibrissin*; in addition, compared with Comparison Examples 4-6, the itching threshold of histamine phosphate was further improved in Examples 1-3 by further controlling the weight fractions of *Astragalus membranacus*, *Radix sileris*, *Rhizoma gastrodiae*, *Calendula officinalis* and *Albizzia julibrissin*.

(2) Eliminating Redness and Swelling-Decreasing Capillary Permeability

The antiallergic function of the actives was investigated by a passive skin allergy model. The antibody and the antigen were combined to cause type I hypersensitivity reaction, resulting in a significant increase in local capillary permeability and the appearance of allergic symptoms such as redness and swelling. It is currently possible to simulate this process in rats, which is an ideal method for studying the antiallergic function of active substances in vivo.

The rat skin, where the type I allergic reaction had occurred and Evans Blue dye was contained, was locally treat by using the traditional Chinese medicine plant composition, so that the function of inhibiting capillary permeability was achieved via the antiallergic function, and thereby the dye content of the local skin was reduced. The dye content was calculated by spectrophotometric method and compared with the model control group (with deionized water instead of the sample) to examine the decrease rate of capillary permeability contributed by the sample.

The decrease rate of capillary permeability by % was calculated according to the formula: capillary permeability reduction rate by $\%/=(T_0-T_n)/T_0*100$, where $T_0$ is the dye content of the model control group, and $T_n$ is the dye content of the sample group. The higher decrease rate of capillary permeability indicates the more pronounced inhibition of allergic response.

Figure 2:
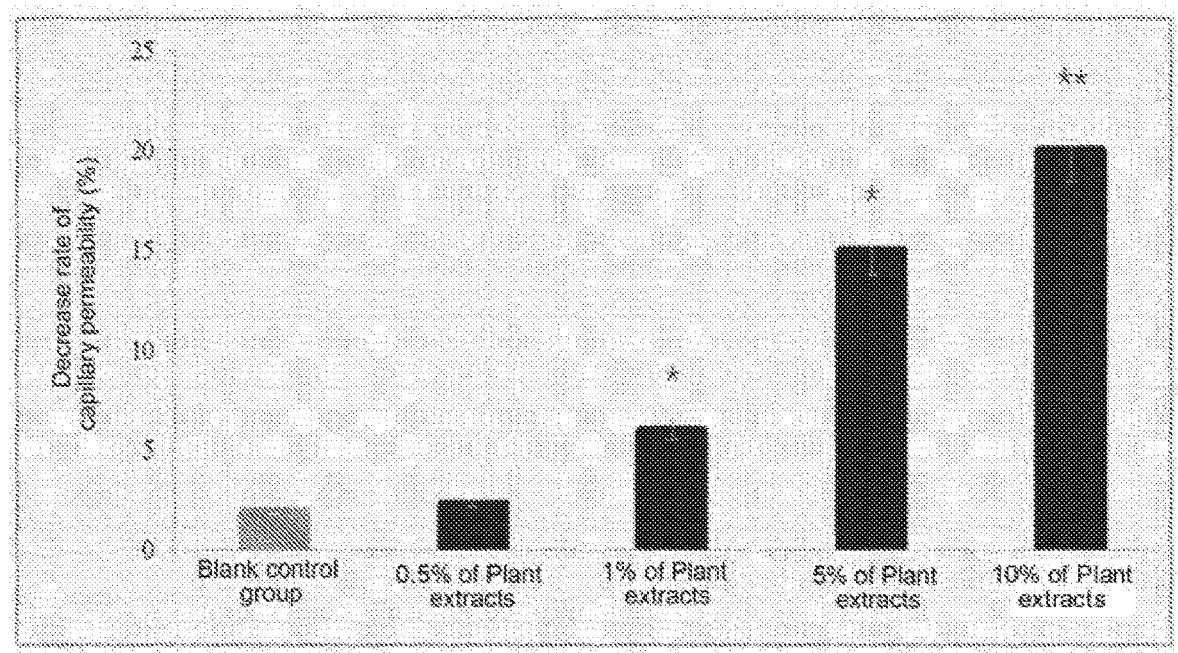
FIG. 2 shows the effect of the traditional Chinese medicine plant composition on the capillary permeability of guinea pigs, wherein * and ** respectively indicate the analysis by SPSS Dunnett-t test is employed.

The results are shown in FIG. 2 and Table 2. As can be seen from FIG. 2, the traditional Chinese medicine plant composition can significantly reduce the capillary permeability of the rat skin during the allergic reaction, effectively alleviate the allergy symptoms, and is positively correlated with the weight concentration, 1%, 5% of Chinese medicine plant composition showed significant difference (p<0.05) compared with the blank control group (formulation matrix, without the Chinese medicine plant composition), wherein 10% of the traditional Chinese medicine plant composition showed extremely significant difference (p<0.01).

In Examples 1-6 and Comparison Examples 1-7 in Table 2, the traditional Chinese medicine plant composition was applied to the itching site at a concentration of 5%, and the results are shown in Table 2:

TABLE 2

|  | Decrease rate of capillary permeability |
|---|---|
| Example 1 | 16 |
| Example 2 | 15 |
| Example 3 | 14 |
| Example 4 | 10 |
| Example 5 | 11 |
| Example 6 | 10 |
| Comparison Example 1 | 3 |
| Comparison Example 2 | 4 |
| Comparison Example 3 | 3 |
| Comparison Example 4 | 5 |
| Comparison Example 5 | 4 |
| Comparison Example 6 | 6 |
| Comparison Example 7 | 5 |

As can be seen from Table 2, compared with Comparison Examples 1-7, the decrease rate of capillary permeability was greatly improved Examples 1-6 by adjusting the ratio of the five components of *Astragalus membranacus, Radix sileris, Rhizoma gastrodiae, Calendula officinalis* and *Albizzia julibrissin*; in addition, compared with Comparison Examples 4-6, the decrease rate of capillary permeability was further improved in Examples 1-3 by further controlling the weight fractions of *Astragalus membranacus, Radix sileris, Rhizoma gastrodiae, Calendula officinalis* and *Albizzia julibrissin*.

(3) Allergy Recovery-Decreasing Skin Water Loss after Allergy

When the skin barrier was damaged by an allergic reaction, the skin moisture would be largely lost; a model of guinea pig skin injury and dehydration was used to simulate the skin water loss after allergy so as to evaluate the functions of allergy recovery and barrier consolidation and protection of the traditional Chinese medicine plant composition. The traditional Chinese medicine plant composition prepared in Example 1 was used in the test, and the composition at a concentration of 1% and 5% was applied to the local damaged skin of the guinea pigs at a dose of 0.1 mL/cm², the change of the water loss of the damaged skin was detected by using a water loss tester, the difference between the groups was compared, and the water loss protection rate was calculated. The laboratory apparatus was: Tewameter TM300, available from CK Company, Germany.

The water loss protection rate by % was calculated according to the formula: water loss protection rate by $\%/=(T_m-T_n)/(T_m-T_c)*100$, where $T_m$ is the data collection value of the water loss of the model control group (deionized water instead of the sample), $T_n$ is the data collection value of the water loss of the sample group, and $T_c$ is the data collection value of the blank control group (no dehydration treatment, with deionized water instead of the sample). The higher water loss protection rate decrease rate indicates the more pronounced barrier repairing effect after allergy.

Figure 3:
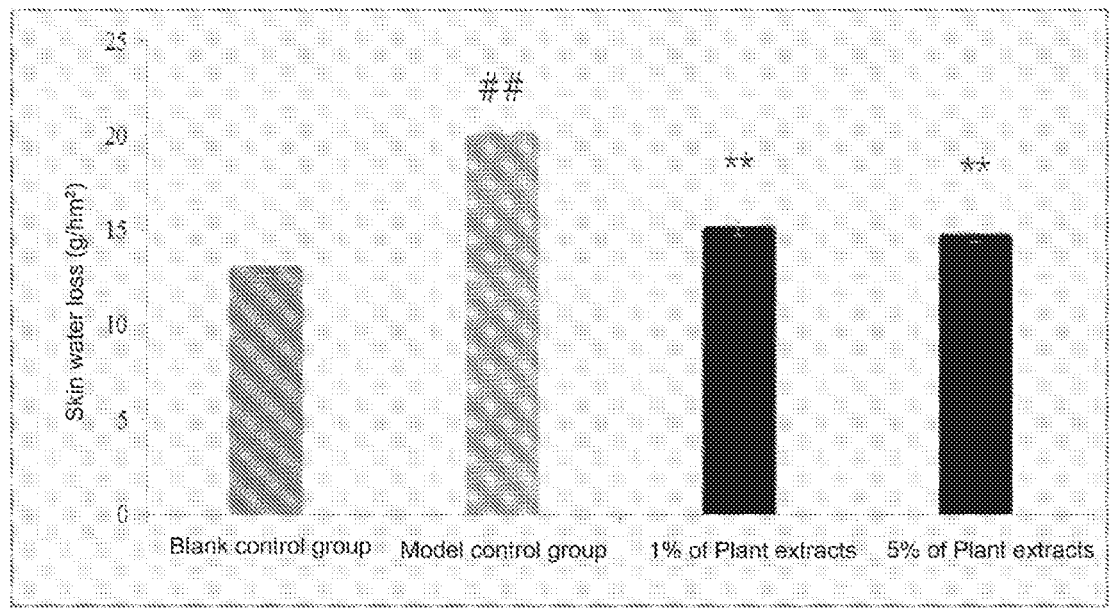
FIG. 3 shows the effect of the traditional Chinese medicine plant composition on the skin water loss of guinea pigs, wherein ## and ** respectively indicate the analysis by SPSS Dunnett-t test is employed.

The test results are shown in FIG. 3 and Tables 3-4.

TABLE 3

| Groups | Skin water loss (g/hm²)) | Water loss protection rate (%) |
|---|---|---|
| Blank control group | 13.0 ± 0.4 | — |
| Model control group | 20.0 ± 0.4 | — |
| Commercially available competitor (amount: 5%) | 19.5 ± 0.5 | 7 |
| 1% addition | 15.1 ± 0.4 | 70 |
| 5% addition | 14.7 ± 0.3 | 76 |

It can be seen from FIG. 3 and Table 3 that the traditional Chinese medicine plant composition can significantly reduce the water loss of the damaged skin of the guinea pig, effectively repair the skin barrier, and these effects are positively correlated with the weight concentration, and have a significant difference ($p<0.01$) compared with the blank control group at an amount of 1% and 5%.

TABLE 4

|  | Water loss protection rate (%) |
|---|---|
| Example 1 | 76 |
| Example 2 | 75 |
| Example 3 | 73 |
| Example 4 | 70 |
| Example 5 | 68 |
| Example 6 | 66 |
| Comparison Example 1 | 15 |
| Comparison Example 2 | 16 |
| Comparison Example 3 | 14 |
| Comparison Example 4 | 18 |
| Comparison Example 5 | 16 |
| Comparison Example 6 | 20 |
| Comparison Example 7 | 22 |

As can be seen from Table 4, compared with Comparison Examples 1-7, the water loss protection rate was greatly improved Examples 1-6 by adjusting the ratio of the five components of *Astragalus membranacus, Radix sileris, Rhizoma gastrodiae, Calendula officinalis* and *Albizzia julibrissin*; in addition, compared with Comparison Examples 4-6, the water loss protection rate was further improved in Examples 1-3 by further controlling the weight fractions of *Astragalus membranacus, Radix sileris, Rhizoma gastrodiae, Calendula officinalis* and *Albizzia julibrissin*.

(4) Security Data

The plant composition and extract preparations were tested for a series of safety tests to confirm from multiple angles that they are safe and non-irritating and applicable to the use of a wide range of people.

1. Multiple (Acute) Skin Irritation Test

The multiple (acute) skin irritation test was carried out by reference to "Safety and Technical Standards for Cosmetics (2015 edition)", and the results showed that the Chinese medicine plant composition was safe and non-irritating at a concentration of 10% or less.

2. Acute Ocular Irritation Test

The acute ocular irritation test was carried out by reference to "Safety and Technical Standards for Cosmetics (2015 edition)", and the results showed that the Chinese medicine plant composition was safe and non-irritating at a concentration of 10% or less.

3. Skin Allergy Test

The skin allergy test was carried out by reference to "Safety and Technical Standards for Cosmetics (2015 edition)", and the results showed that the Chinese medicine plant composition had no allergenicity at a concentration of 10% or less.

4. Phototoxicity Test

The 3T3 neutral red intake phototoxicity test was carried out by reference to "GB/T 21769-2008 Chemical-In vitro 3T3 Neutral Red Uptake Phototoxicity Test Method", and the plant composition is expected to be non-phototoxic.

5. Human Skin Patch Test

The human skin patch test was carried out by reference to "Safety and Technical Standards for Cosmetics (2015 edition)", and the results showed that the Chinese medicine plant composition had no adverse reaction to the human body at a concentration of 10% or less.

6. Erythrocytes Hemolysis and Coagulation Test

The erythrocytes hemolysis and coagulation test was carried out by reference to Red Blood Cell Test System provided by European Centre for the Validation of Alternative Methods, ECVAM, and the results showed that the Chinese medicine plant composition had no adverse reaction to the human body at a concentration of 10% or less.

Example 7

A skin care product was prepared from the traditional Chinese medicine plant composition prepared by Example 1, comprising in percentages by mass:

| the adjuvant phase A: | |
| --- | --- |
| xanthan gum | 0.06% |
| glycerol | 2% |
| the adjuvant phase B: | |
| glyceryl stearate | 2.3% |
| cetearyl alcohol | 1% |
| pentaerythritol distearate | 1.6% |
| hydrogenated polyisobutylene | 3% |
| octoic acid | 3% |
| poly dimethyl silicon | 2% |
| isostearyl isostearate | 3% |
| the adjuvant phase C: | |
| methyl isothiazolinone | 0.06% |
| phenoxyethanol | 0.4%; |
| the traditional Chinese medicine plant composition prepared by Example 1 with the balance being water. | 10%; |

A preparation method of the skin care product, comprising the following steps:

(1) the xanthan gum in the adjuvant phase A was added to the glyceryl and evenly blended, and heated to 80-85° C.;

(2) the raw materials of the adjuvant phase B were mixed, and heated to 80-85° C.;

(3) all the adjuvant phase B of the step (2) was added to the adjuvant phase A of the step (1), homogenized at 3000 r/min for 5-10 min, heated to 80° C. and stirred for 20-40 min following by starting cooling at a cooling rate of 1-2° C./min by stirring at a stirring rate of 30-50 r/min;

(4) when the temperature was lowered to 45° C., the adjuvant phase C and the traditional Chinese medicine plant composition prepared by Example 1 were added, stirred evenly, and continued to cool to below 38° C. to obtain the skin care product.

Example 8

The skin care product comprises in percentages by mass:

| the adjuvant phase A: | |
| --- | --- |
| xanthan gum | 0.08% |
| glycerol | 3% |
| the adjuvant phase B: | |
| PEG-100 stearate | 3% |
| cetearyl alcohol | 1.5% |
| pentaerythritol distearate | 2% |
| hydrogenated polyisobutylene | 4% |
| capric triglyceride | 4% |
| poly dimethyl silicon | 3% |
| isostearyl isostearate | 4% |
| the adjuvant phase C: | |
| iodopropynyl butylcarbamate | 0.08% |
| ethylhexylglycerin | 0.8%; |
| the traditional Chinese medicine plant composition prepared by Example 1 with the balance being water. | 5%; |

The preparation method is the same as that of Example 7.

Example 9

| the adjuvant phase A: | |
| --- | --- |
| xanthan gum | 0.02% |
| glycerol | 1.5% |
| the adjuvant phase B: | |
| glyceryl stearate | 2% |
| cetearyl alcohol | 0.5% |
| pentaerythritol distearate | 1% |
| hydrogenated polyisobutylene | 2% |
| capric triglyceride | 2% |
| poly dimethyl silicon | 1% |
| isostearyl isostearate | 2% |
| the adjuvant phase C: | |
| methyl isothiazolinone | 0.02% |
| ethylhexylglycerin | 0.2%; |
| the traditional Chinese medicine plant composition prepared by Example 1 with the balance being water. | 0.5%; |

The preparation method is the same as that of Example 7.

Anti-Allergy Skin-Improving Sensitive Skin State in Five Dimensions

When the skin is sensitive, it is often accompanied by itching, redness, tension, pricking and other unpleasant feelings. Thirty subjects aged 20-55 years old who reported themselves with skin sensitivity were randomly divided into two groups, 5% of the anti-Allergy cream and 5% of commercial competitor cream were applied onto their faces respectively. Use feedback from the subjects were collected before use and 4 weeks after use in the form of questionnaires to visually evaluate the anti-Allergy and improving functions of the traditional Chinese medicine plant compositions on sensitive skin in five dimensions of relieving itching, eliminating redness, eliminating swelling, eliminating tension and eliminating pricking.

Figure 4:
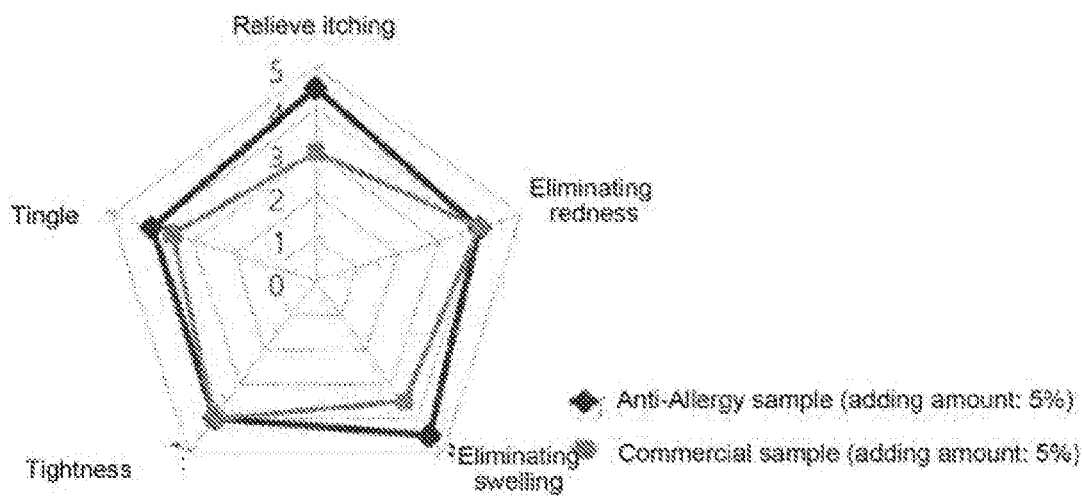
FIG. 4 shows the improvement of sensitive skin by the skin care product prepared from the traditional Chinese medicine plant composition of the present invention in five dimensions.

The result is shown in FIG. 4, and the traditional Chinese medicine plant composition added in an amount of 5% can improve the sensitive state of the skin in five dimensions of relieving itching, eliminating redness, eliminating swelling, tension and pricking.

In summary, the traditional Chinese medicine plant composition of the present application achieves the function of anti-Allergy sensitive skin through three ways of "anti-Allergy itching, eliminating redness and swelling, and allergy recovery" by employing the dsynergistic effects of the five components including stragalus membranacus, *Radix sileris, Rhizoma gastrodiae, Calendula officinalis* and *Albizzia julibrissin* and according to the idea of "integral, syndrome differentiation and comprehensiveness" of traditional Chinese medicine.

The applicant declares that the present invention is described in detail by the above-described embodiments, but the present invention is not limited to the above detailed process equipment and process flows, that is, it does not mean that the present invention must be implemented in accordance with the detailed process equipment and process flows described above. It will be apparent to those skilled in the art that any modifications of the present invention, equivalent substitutions of the materials for the product of the present invention, and additions of auxiliary ingredients, selections of the specific means and the like, are all within the protection and disclosure scopes of the present invention.

What is claimed is:

1. An ethanolic extract from a plant composition, wherein the plant composition consists of in parts by weight: 20-60 parts of *Astragalus membranacus*, 10-30 parts of *Radix sileris*, 10-30 parts of *Rhizoma gastrodiae*, 5-20 parts of *Calendula officinalis*, and 5-15 parts of *Albizzia julibrissin*.

2. The ethanolic extract from the plant composition according to claim 1, wherein the plant composition consists of in parts by weight: 30-50 parts of *Astragalus membranacus*, 15-25 parts of *Radix sileris*, 15-25 parts of *Rhizoma gastrodiae*, 8-15 parts of *Calendula officinalis*, and 5-10 parts of *Albizzia julibrissin*.

3. The ethanolic extract from the plant composition according to claim 1, wherein the plant composition consists of in parts by weight: 35-45 parts of *Astragalus membranacus*, 18-25 parts of *Radix sileris*, 18-25 parts of *Rhizoma gastrodiae*, 12-15 parts of *Calendula officinalis*, and 6-10 parts of *Albizzia julibrissin*.

* * * * *